United States Patent [19]

Fink et al.

[11] Patent Number: 5,510,066
[45] Date of Patent: Apr. 23, 1996

[54] METHOD FOR FREE-FORMATION OF A FREE-STANDING, THREE-DIMENSIONAL BODY

[75] Inventors: David J. Fink, Shaker Heights; Thomas J. Ward, Columbus; Joel C. Preston, Grove City, all of Ohio

[73] Assignee: Guild Associates, Inc., Columbus, Ohio

[21] Appl. No.: 317,892

[22] Filed: Oct. 4, 1994

Related U.S. Application Data

[63] Continuation-in-part of Ser. No. 929,449, Aug. 14, 1992, Pat. No. 5,370,692.
[51] Int. Cl.[6] .................... B29C 41/02; B29C 41/52
[52] U.S. Cl. .................... 264/40.1; 156/64; 156/242; 156/307.1; 264/240; 264/255; 364/468; 364/476; 395/119; 427/8; 427/399; 427/421; 427/424; 427/427
[58] Field of Search .................... 264/22, 25, 40.1, 264/240, 308, 255; 156/64, 242, 307.1; 427/8, 399, 400, 421, 424, 427; 364/468, 476; 395/119

[56] References Cited

U.S. PATENT DOCUMENTS

| | | | |
|---|---|---|---|
| 4,665,492 | 5/1987 | Masters | 364/468 |
| 5,204,055 | 4/1993 | Sachs et al. | 264/25 X |

*Primary Examiner*—Leo B. Tentoni
*Attorney, Agent, or Firm*—Frank H. Foster; Kremblas, Foster, Millard & Pollick

[57] ABSTRACT

A preparing of a self-supporting or free-standing three-dimensional unitary structural body by a method including generating successively a plurality of cross-sectional layers of the body, one layer top of the other and with the layers joined together to form the body and with the generating of a cross-sectional layer comprising placing a plurality of drops of a liquid composition, containing a first reactant, in a pattern of discrete drops making up the cross-sectional layer and subsequently placing a plurality of discrete drops of other liquid composition, containing another reactant, in contact with the placed drops ion the pattern so that the first reactant and the other reactant react to provide a solid.

21 Claims, 3 Drawing Sheets

METHOD FOR FREE-FORMATION OF A FREE-STANDING, THREE-DIMENSIONAL BODY

This application is a continuation-in-part application of Ser. No. 07/929,449, filed Aug. 14, 1992, now U.S. Pat. No. 5,370,692, issued Dec. 6, 1994.

TECHNICAL FIELD

This invention relates to free-formation of a self-supporting, or free-standing, three-dimensional unitary structural body (Free Form Manufacturing or FFM). More particularly, the invention concerns preparing a substantially inorganic body by a "rapid prototyping" or like system which includes localized reaction of reactants in deposited discrete liquid drops deposited from liquid compositions as patterned drop configurations for providing successive cross-sectional planar-like layers of the structural body to build up cross-sectional layer-by-layer, one upon another, and thus create the free-standing, three-dimensional structural body. With greater particularity, the invention concerns a method of providing successively respective individual cross-sectional layers making a free-standing three-dimensional structural body comprised of a laminar-like integrated-layered structural body by first placing liquid drops of a fluid composition containing a first reactant in a discrete-drop pattern of a cross-sectional layer being prepared and subsequently placing liquid drops of an other fluid composition containing a second reactant in a discrete-drop pattern with deposited liquid drops of the other composition contacting the earlier deposited liquid drops and with the second reactant reacting with the first reactant to provide a planar cross-sectional layer and thereafter successively repeating this sequence to provide an adjacent planar cross-layer on top of the earlier prepared planar layer with the adjacent planar layer integrated, or joined, to its earlier prepared layer and with a plurality of successively prepared layers comprising the free-standing three-dimensional structural body.

BACKGROUND ART

In the design and production of prototype parts for articles of manufacture as well as for preparation of various thermal and electrical insulators, and also patterns, dies and molds for investment casting, during the past several decades there has arisen a number of systems and processes termed "rapid prototyping" or desk top manufacturing or free form manufacturing (FFM) or the like. A number of these systems primarily rely upon preparing sequential cross-sectional layers of the desired three-dimensional object with sequential cross-dimensional adjacent layers integrated together as successive laminae to fabricate the three-dimensional laminar-like structural object.

Illustrative of one such rapid prototyping method is that of fabricating three-dimensional objects by stereolithography, such as described in U.S. Pat. No. 4,575,330, C. W. Hull. That patent teaches a generating of three-dimensional objects by creating a cross-sectional pattern of the object to be formed at a selected planar surface of a fluid medium capable of having its physical state altered by impinging radiation or the like, for changing of the pattern on the fluid surface to a solid planar-like cross-section and then successively forming corresponding successive adjacent cross-sections of the object on top thereof with successively-created adjacent cross-sections integrated together into a laminar-like build-up of the desired object.

Additional rapid prototyping and desk-top manufacturing and the like systems are described, for example in "Mechanical Engineering", April 1991, pages 34–43, in a Special Report entitled "Rapid Prototyping Systems" and in the "Tool And Manufacturing Engineers Handbook", Fourth Edition, Volume VI, 1992, Chapter 7, pages 7–9 to 7–26, entitled "Rapid Prototyping".

Many of the taught systems now in commercial practice, or under development, produce resinous polymeric articles from liquid monomers or polymer powders involving technologies of laser induced polymerization, broad-spectrum light initiated photopolymerization, selective laser powder sintering and the like. Only two art systems appear to be applicable to free-forming a body of an inorganic substance, such as a ceramic or the like. One of these systems in forming layers, would selectively sinter directly a pattern on an inorganic powder surface by a laser, or would indirectly selectively sinter a pattern of a lower melting point binder material admixed with the inorganic powder, and then by repetition build-up sintered layers of the pattern into the object. Another system would use ink jet printing technology to bind a layer of ceramic particles together by selective application of a binding medium to the inorganic particles and by repetition build up cross-sectional layers into the formed body or structure. ("Proceedings of the Solid Free-Form Fabrication Symposium", Univ. of Texas, 1990, M. J. Cima and E. M. Sacks, "Three-Dimensional Printing: Form, Materials and Performance", p. 187–194).

Included in the just-described rapid prototyping and desk-top manufacturing systems for fabricating prototypes and other bodies are computer aided design (CAD) and computer aided manufacturing (CAM) technology. For example, in the just-mentioned U.S. Pat. No. 4,575,330, one may use various principles of computer generated graphics so as to produce designed three-dimensional objects directly from computer instructions. Thus, the sought structural body may be designed through CAD by a computer operator using computer-aided graphics and functions of the computer to design and/or sculpture a desired three-dimensional model or prototype body or the like whose image memory can be displayed on a computer screen (CRT) for subsequent review and modification, if desired. Thereafter, the computer through CAM can create mathematical sections or slices of the designed three-dimensional model of the object into successive adjacent cross-sectional layers, and by CAM instruct a making by a specific technology of the object represented by the image. For example, as taught by the aforementioned patent, CAM will cut the image of the CAD-designed body or prototype into multiple successive cross-sectional layers and issue the operating instructions and parameters for successively forming by stereolithography the successively adjacent cross-sectional layers one on top of another with the layers integrated into a laminar built-up structure of the desired body of polymerized resin.

Depending on the particular compositions and materials used in fabricating various bodies by the particular rapid prototyping, desk-top manufacturing or free-form manufacturing or like procedures, the various fabricated bodies are useful in a variety of applications. A natural application is the creation of a concept model so that a designed part can be touched and examined and reviewed for aesthetic purposes and possibly tested for its fit, its ergomatic feasibility and the like utility requisites. Where a limited production of several to a few models are needed, the economics of fabrication may be even more favorable than using more elaborate tooling for fabrication. Models and prototypes thus can be evaluated and their parameters and dimensions altered and finalized for further evaluation and testing of the altered bodies. Some other illustrative utilities for various generated bodies from various materials include: calcium phosphate and hydroxylapatite materials to generate customized bodies for orthopaedic hard tissue implants; solid-liquid porous filters of various particulate materials bound together by sintering after a burn-off removal of an initial fugitive adhesive binder; heat and electrical solid insulators; as well as ceramic cores and shells for metals casting and for other purposes from alumina with colloidal silica binders or of predominantly silica or refractory inorganic oxides; and the like.

BRIEF DISCLOSURE OF INVENTION

The method of the invention comprises in general a preparing of a free-standing three-dimensional structural body, which in finished state consists essentially of inorganic material by successively generating by a successive drop placement technology of adjacent cross-sectional planar-like layers of the body with a successively freshly generated layer on top of an adjacent earlier generated cross-sectional layer and with earlier and later generated layers integrated as a whole to comprise the prepared free-standing, three-dimensional structural body. Specifically the invention includes depositing of earlier and later generated cross-sectional layers successively by applying to a support surface of a plurality of individual liquid drops of liquid compositions containing one or more reactant species. The applying of the drops is as discrete individual drops arranged in a pattern corresponding to a planar-like cross-sectional layer of the body being prepared and then followed with an applying onto and joining and/or overlapping the earlier applied plurality of individual liquid drops of the first composition with a plurality of liquid discrete drops of an other liquid composition containing an other reactant, which other reactant is such upon contacting the reactant in the liquid drops of the earlier applied composition that the reactant and other reactant react to form an inorganic material.

In the method of the invention desirably and preferably the applied drops of the liquid composition and another liquid composition in addition to reactant, also contain inorganic substance dissolved and/or dispersed or suspended as solid particles therein, and optionally may contain other materials (not necessarily inorganic), such as a viscosity enhancer, a resinous binder substance, or like material to facilitate practice of the method of the invention and formation of the structural body. Thus, as apparent later herein, the liquid compositions providing the applied drops may contain dissolved, dispersed or suspended particles of the same or different composition of the solid(s) resulting from reaction of the reactants in the applied drops.

Additionally, the support surface onto which are deposited an initial pattern of drops as well as a later pattern of drops to generate the initial cross-sectional layer of the body desirably is adapted to facilitate liquid removal from applied drops, such as by being porous to absorb by capillarity or to wick away liquid from the deposited drops.

In an idealized practice of the invention computer aided design (CAD) and computer aided manufacturing (CAM) technology are employed with CAD utilized to design and screen-view and revise a desired body to be prepared and with CAM utilized to slice the desired designed body in appropriately sized cross-sectional layers and also to manipulate apparatus element and to control parameters of various liquid drop size and their placements and the like during the creation of the free-standing, three-dimensional structural body.

BRIEF DESCRIPTION OF DRAWINGS

In the figures, the same number is used to designate the same, or equivalent, or like method steps and/or features with prime-markings therefore in respective successive figures.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, with regard to drops, the words placed or deposited or terms similar thereto are often used. They are not limited to deposition by gravity but include placement through other means, such as forceable spray, electrical attraction, etc., where such means are known as being useful for liquid drop placement by those skilled in the art.

DETAILED DESCRIPTION

Figure 1:
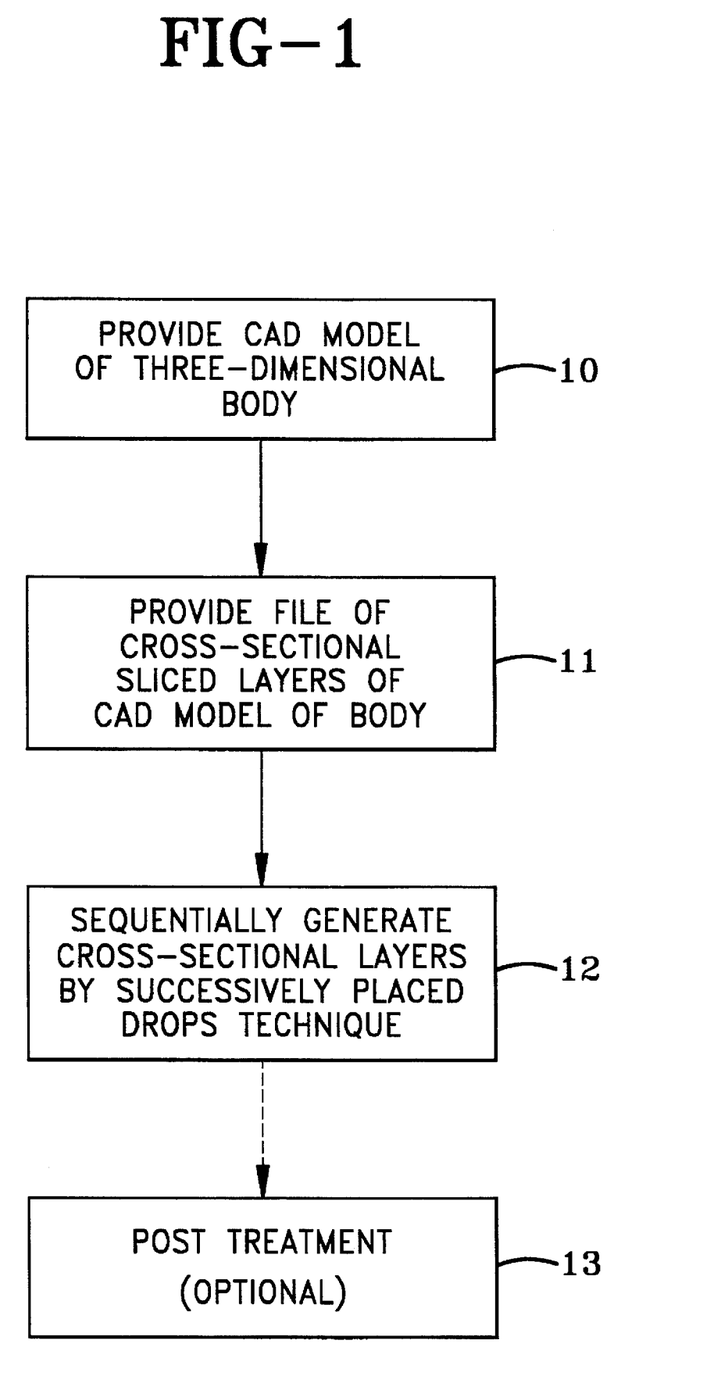
FIG. 1 provides an overall sequential schematic block-like presentation of successive steps for preparation by a rapid-prototyping technique including computer CAD and CAM technologies to manufacture a self-supporting or free-standing three-dimensional structural body.
Figure 2:
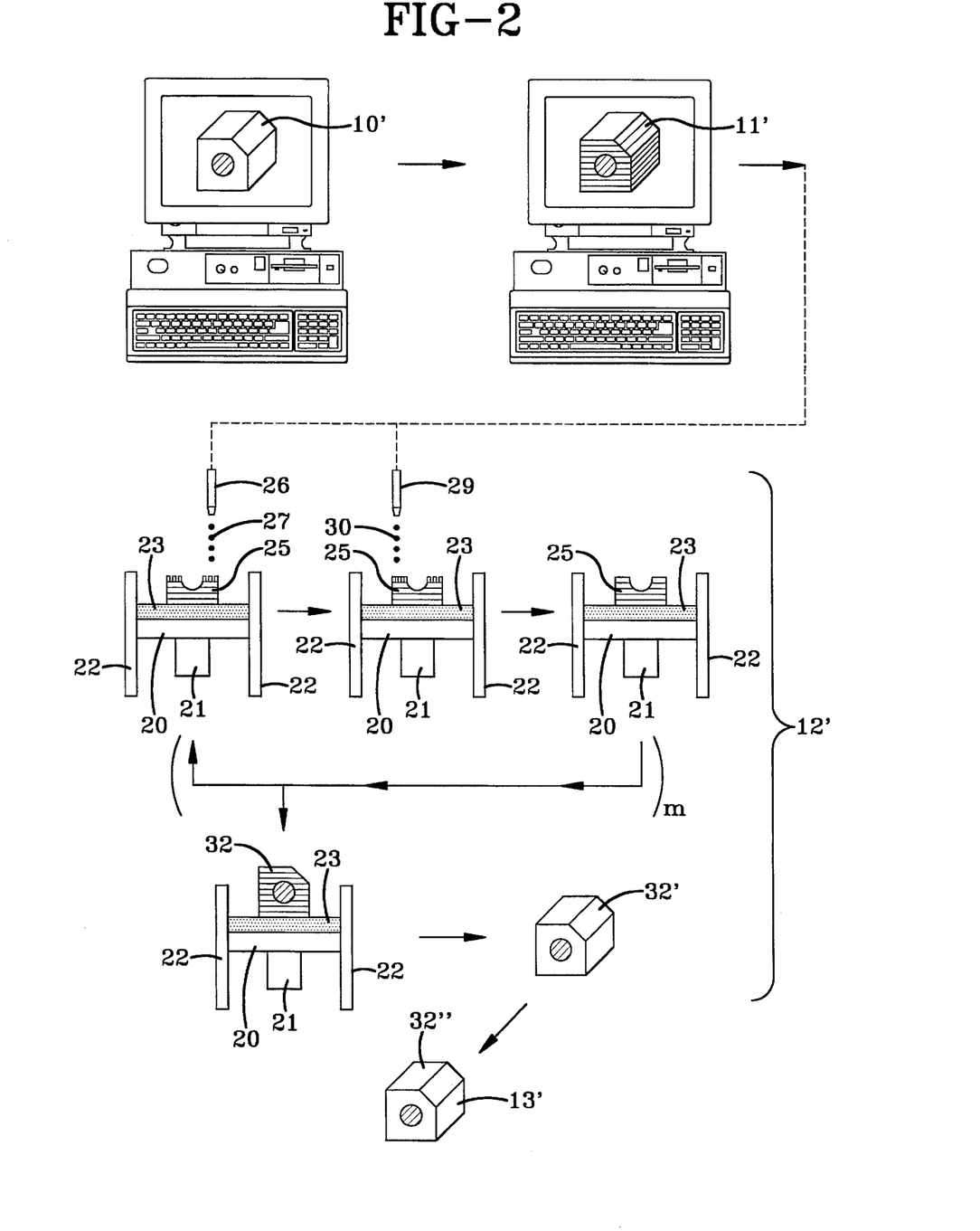
FIG. 2 presents, in an essentially schematic-type format, various successive steps for the rapid-prototype method technique utilizing CAD and CAM technologies to manufacture a free-standing, three-dimensional structural body and with greater schematic detail given for the instant invention's successive-drop-technique generation and integration of adjacent cross-sectional, planar-like layers into a desired free-standing, three-dimensional structural body.
Figure 3:
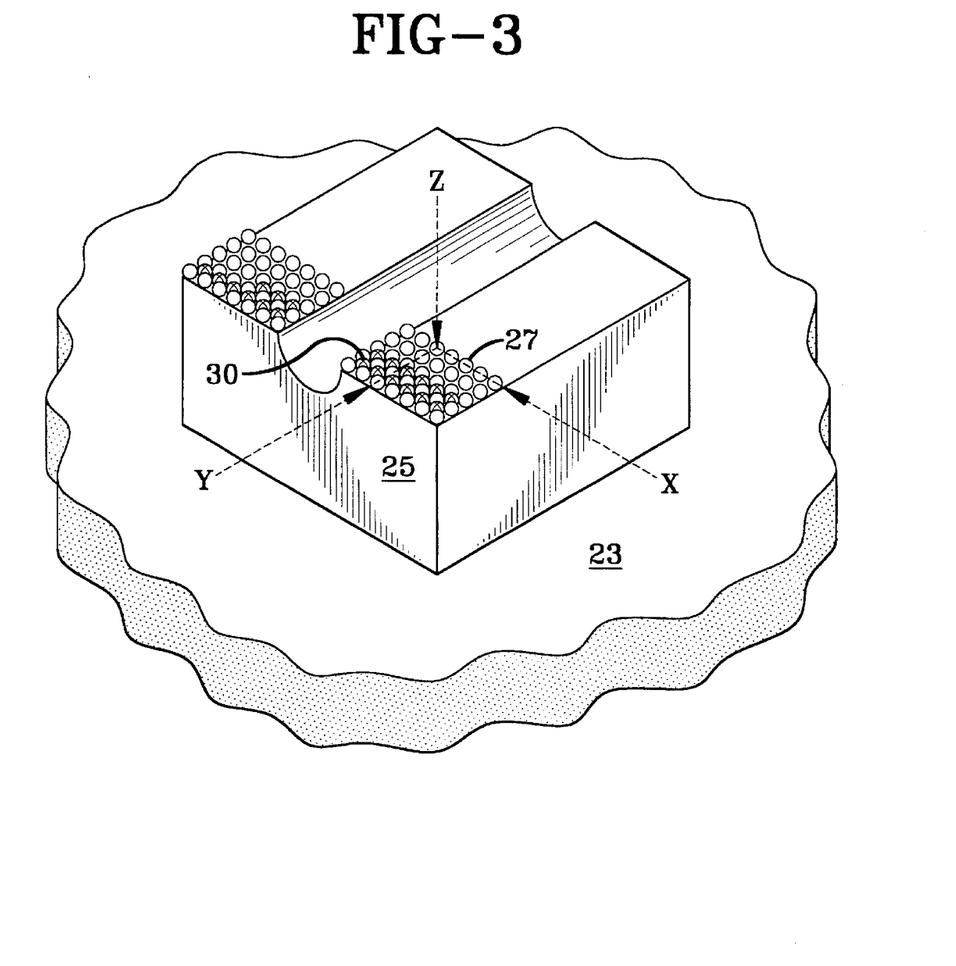
FIG. 3 illustrates, in perspective view, a sectional portion of a being-prepared partial free-standing, three-dimensional body sectioned at a location of an earlier prepared integrated cross-sectional layer of the body and with this earlier prepared layer being a support surface upon which is illustrated a partial formation of the next adjacent cross-sectional layer being generated.
Figure 4:
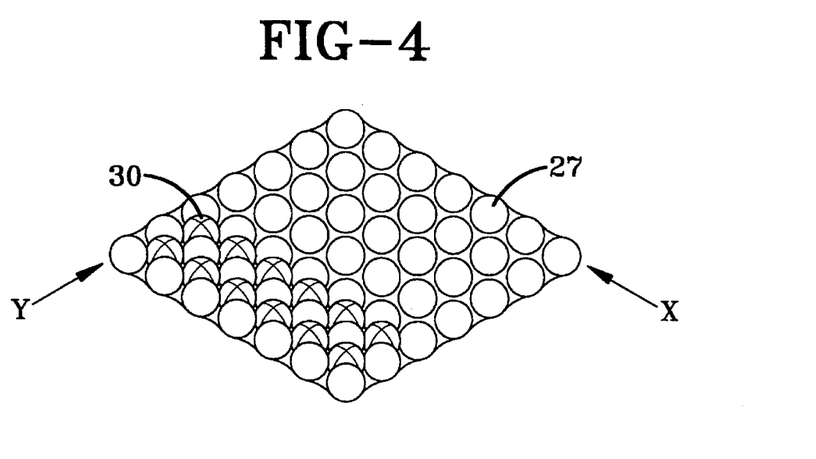
FIG. 4 illustrates a planar partial view of a top corner, taken on coordinate axis lines X and Y, of the top portion of the being-prepared layer portion of the free-standing, three-dimensional structural body shown in FIG. 3.

In the schematic illustrated process and/or system shown in FIGS. 1 and 2, 10 and 10', respectively, represent an initial step (10) of origination of and/or a design or structural model or body (10'), capable of being visualized on a CRT screen, of a free-standing three-dimensional structural body desired to be generated. For example, in FIG. 1 the design may be from an original concept (e.g. created) by computer-aided design techniques using computer aided graphic programs and the like and created, when desired, to provide and to conform to designated parameters, including shape, size and dimensions, for CRT display. Alternatively, an earlier (e.g. manually sculptured or fabricated model or body) may be probe scanned and/or its shape, parameters, etc. transferred and entered into the computer memory bank so as to be subsequently capable of display and visualization on a CRT screen. In FIG. 2 one such structural body, designated 10', for example is shown schematically as a pentagonal-sided short bar having an about centrally located cylindrical hole running longitudinally therethrough, displayed on a schematically represented computer CRT screen.

Commercially available are computers and CAD systems and softwares from which selection readily can be made for practice of the initial step in a practice of an overall process of multiple steps for practicing the invention. Skill of the computer operator is of importance, but with practice and experimentation it is well within the skill of the art to accomplish in the overall process this initial step of providing a computer memory file of a computer aided design model of the three-dimensional structural object or body to be fabricated.

In FIGS. 1 and 2, 11 and 11' respectively, schematically designate a following step (11) and/or sliced result (11') of this following step, wherein the computer's memory bank stored file of the design or structural model or body desired to be generated now has been sliced into a plurality of cross-sectional (planar-like or relatively two-dimensional) slices for subsequent utilization in the next step, 12 and 12', of essence to applicant's invention.

The particular or specific number of cross-sectional slices and their thickness is dependent on parameters and materials employed in the next-to-follow step. In the current state of FFM applications, one finds cross-sectional layer thicknesses ranging from 0.0005 to 0.0015 inch (0.0127 mm to 0.0384 mm) to have utility. Obtaining this degree of resolution with the invention will involve optimizing device design such that materials, particle sizes, drop sizes, drop nozzle sizes, will permit the resolution to be accomplished. This degree of resolution is expected to be readily obtainable without undue experimentation by one of ordinary skill in the FFM art in view of this application's teachings of the invention. Of course, subsequently placed smaller drops and more drops placed per unit area generally provides smaller layer thicknesses along with improvement in resolution and control of dimensions of the being-formed body and are to be expected to be very desirable and useful.

Commercially available are computers and programs (e.g. CT technology) and software for appropriate slicing into the desired plurality of cross-sectional slices of a desired thickness of the computer-aided design model of the three-dimensional object or body to be generated and it is within the ordinary skill of one in the art without undue experimentation to arrive at requisite parameters and to so create a computer memory file of sequential adjacent sliced (cross-sectional) layers of the structural object or body to be fabricated.

In FIGS. 1 and 2, the next illustrated step involves an overall generation and integration step (12 and 12') of the computer file of sequential cross-sectional adjacent layer slices into a desired structural body (32'). FIG. 2 in a more detailed schematic presents the multiple layer slice generation and integration step (12') including the invention's unique successive drop placements of liquid drops 27, containing a first reactant, in a pattern followed by placement of contacting drops 30 containing another reactant in an overlying contacting pattern.

With reference to FIG. 2, there is schematically shown a movable support base 20, such as an elevator platform adjustable to be moved to an up or down location by means of a ram 21 and by a mechanical, hydraulic or like movement means, not shown. The support base 20 moves within guide slides 22 to better control the support's movement alignment and placement.

Although in FIG. 2 the support base 20 and ram 21 and slides 22 are shown for upward and downward movement, depending upon the particular drop application means being employed and its location as well as the specific or particular configuration of the body to be generated, the location placement of 20, 21 and 22 can be at various vertical angles, even as far as sideways (horizontal) and even to provide for upward movement and upwardly or angularly deposited drop applications depending on particularly employed drop application means and the specific compositions of the first and another liquid drops.

Resting upon movable support base 20 is a, generally attached thereto, porous support base 23, upon which, by the invention's successive drop applications, there is created an initial planar-like cross-sectional layer of the three-dimensional body to be generated. The support base 23 is illustrated as porous so that it better may wick away (e.g. by capillary action) liquid from subsequently applied drops 27 and 30.

Not illustrated, but contemplated as useful, are other means such as for placing a reduced pressure on the porous support base 23 to faster remove and/or wick away liquid. Conventional faucet-water aspirator means, such as useful in suction filtration, or mechanical pumps for reduced pressure generating means, also not illustrated, could by one of ordinary skill be installed, attached, and adapted so that the porosity in support base 23 is at a reduced pressure and thus adapted to expedite liquid removal from applied drops 27 and 30. In lieu of, and/or in combination therewith, other and additional means to expedite liquid removal may be incorporated. For example, heating means, such as sealed electrical resistance elements, not illustrated, within porous support base 23 and/or support base 20, could be utilized so as to vaporize liquid from applied drops, and when so employed desirably would be accompanied by installed duct work (not illustrated) and by forced withdrawal fan ventilation means or the like (not illustrated) adapted to withdraw liquid vapors from the vicinity of drop's applications upon the placed or deposited drops being heated. Such heat also could expedite reaction of the reactants. Other means and techniques for facilitating liquid removal from applied drops will be apparent to the art and also are considered within the scope and intent of the invention.

As schematically illustrated in FIG. 2, under 12' step, there is shown a partially generated body 25 of the illustrated multi-cross-sectional CRT displayed body 11' (step 11) of the to be generated illustrated body 10' (step 10) of a pentagonal-sided short bar having an about centrally located cylindrical hole longitudinally therethrough. The partially generated body 25 in its far left presentation is at a midway point of generation or fabrication so that illustrated is the partially formed body at a process of preparation of an about vertically half-way-located cross-sectional, horizontal layer upon an earlier prepared underlying horizontal cross-sectional layer by depositing and/or placing in a designated pattern of the being formed cross-sectional layer of a plurality of drops 27 of a fluid composition by a not illustrated dispensing or depositing means through a deposit outlet means, such as a nozzle 26. Following the patterned depositing of drops 27 in its farthermost left presentation of partially generated body 25, there is shown movement by an arrow to a centrally located presentation of partially generated body 25 (now having a patterned plurality of drops 27 thereon) upon which there now is deposited and/or placed a patterned plurality of drops 30 of the another liquid composition from a not illustrated dispensing or depositing means, through a deposit outlet means, such as nozzle 29. In the farthermost right presentation (movement thereto shown by an arrow) of body 25 and of its accompanying (ancillary for the generation step) elements 20, 21, 22 and 23, used during the body's generation, body 25 is shown with the particular cross-sectional layer formed, as shown in the central and far left presentations, as being formed under applicants' drop depositing process. Of course, in the central illustration of partial body 25, the patterned drop 30 application is so aligned with the earlier placed patterned drop 27 application that the two applications contact in a manner adapted for reactants in the drops to contact, generally overlap, to react with the formed reaction product to become a solid which integrates with an earlier prepared underlying layer.

In the far right illustrated location, the reaction between the reactants in the applied first drop composition and the applied second or another drop composition continues to proceed to a movably-complete state of a cross-sectional layer from which significant and substantial liquid content of the applied drops has flowed and/or by other means been removed, although the just prepared cross-sectional layer may still be liquid-moist and or pasty-like in consistency. At this stage in step 12' for preparation of a next on top cross-sectional layer, the movement (shown by directional arrows) of partial body 25 and its ancillary accompanying elements is to the initial far left position wherein a patterned depositing of drops 27 again would be made and followed by movement therefrom to the central position wherein a patterned depositing of drops 30 again would be made before moving to the far right position. Thereafter this sequence is repeated, such as for (n) times, where n represents the total of the successively prepared cross-sectional layers making up the generated body, now designated 32. The body 32 at this completion stage of step 12' preparation can be deemed to have green strength, depending on the extent of liquid removal therefrom, the extent of progression of the reaction of the reactants with each other, the nature of the components of the compositions including therein the amount, type, size and like of dispersed material, including binders, viscosity-enhancers and the like, with adequate green strength invariably reached relatively quickly to a strength value permitting removal of body 32 from porous support 23 and upon drying further with or without a heating means (not illustrated) to become substantially reaction-complete, or dry enough, now to be designated body 32'.

Although FIG. 2 for step 12' illustrates movements of the being generated body 32 and 32' to various locations, such as left-to-right horizontal movement and upward and downward vertical movement to various locations for procedural drop application of one composition, followed by drop application of another application, and to a location, if needed, for drying and/or reaction completion before movement for repetition of this sequence, all such movement is relative and is to be so understood. Thus movement also may be right to left. Also porous support 23 and its ancillary positioning elements and the being prepared partial body 25 may be held in a stationary position and instead movement may be made of deposit outlet means 27 and 29 to provide requisite positioning for applications of drops 27 and 30 and a drying/reaction period before repeating the cycle and generating a successive cross-sectional layer upon an earlier generated layer. Likewise as mentioned earlier, depending on specific components in the compositions of the drops, the particular drop application means, and the like, the illustrated schematic position location can be at various angles from horizontal and vertical such as even may be needed for a specific particular structural configuration of the to-be-generated structural body.

As will be discussed later, depending on the generated body 32', its green strength, the component materials comprising the body 32' and the like, body 32' optionally may be processed further from step 12' through any of numerous procedures to be discussed later in a step designated 13 and 13' respectively in FIGS. 1 and 2, to provide an optionally processed generated body 32" having properties even more desirable or requisite and compatible for its end utility application.

Although as will be apparent from the examples presented herein, one may practice the invention by manual and individual means and also visualize by eyesight the specific free-standing three-dimensional body to be generated and the same as divided into a plurality of cross-sectional layers for guidance in the practice and employ relatively crude drop-dispensing means, such as micropipettes, and filling and positioning by-hand means, such as manual filling of the pipettes and moving them to requisite locations and dispensing of drops, it is contemplated that more ideally more sophisticated technological means will be employed. For example, computer aided design (CAD) and computer aided manufacturing (CAM) and programs therefor are contemplated techniques for applying the capabilities of computers to the processes of designing and manufacturing. It is contemplated to harness the principles of computer aided graphics with CAD and CAM to execute the steps set forth in FIGS. 1 and 2. Some teachings of application of such computer technologies can be found in the aforementioned U.S. Pat. No. 4,575,330 for usage with UV curable plastic and by the stereolithography "prototyping" process. Additional details and information teaching such computer practices also can be found in "Manufacturing Engineering", November 1991, pp. 77–79, "The Real Cost of Rapid Prototyping", by Terry T. Wohlers. Specifically taught in this journal article are a number of commercially available computers and programs and the like for proceeding through steps 10 and 10' and 11 and 11' of FIGS. 1 and 2, respectively.

For proceeding through step 12 and 12', respectively, of FIGS. 1 and 2 in place of the micropipettes employed in a soon to be described Example I, it is contemplated that there be employed apparatus of the nature of and/or closely akin to ink-jet printers used in computer technology with little to no modification thereof of commercially available ink-jet printers being needed for practicing step 12 and 12'.

An ink jet printer functions by supplying a drop-on-demand of an ink composition to a printing surface. One type, called a "bubble jet", functions by having ink from a reservoir supplied to a tiny tube and having an electrical resistance in contact with the tiny tube. Upon a designated demand, an electrical current passes through the resistance and ink in the tube is heated. As the ink heats, a portion near the heater vaporizes and expands, pushing a drop of ink from the nozzle of the tiny tube. The vaporizing in the tube creates a bubble and upon the bubble contracting, after the ink drop is expelled and released, there is created a drop in pressure that pulls more ink into the tube. Thereafter a reactivation of the resistance heater permits a new drop to be ejected. With an apparatus element arrangement of a plurality of tiny tubes and their directed nozzles, and with the resistance heaters operated as dictated and controlled by the computer, one can rapidly deposit to print characters in numerous fonts, graphics, and the like with dot resolutions from a few drops per inch (e.g. 6–10 drops per inch wide by 6–10 drops per inch high) to higher resolutions, such as 360 by 360 dots per inch (dpi) height and width per font character printed. Another useful type of an ink jet printer employs for activation a piezoelectrical means to displace and eject a drop of ink from the nozzle of the tiny tube.

Whatever modification(s) of commercial ink jet printers that may be needed appear to be within the skill of the art to make and would involve only aspects such as mounting the employed ink jet printer(s) in a requisite positional or traveling location relationship to a porous support surface 23, to have a printer's ink jets' nozzles, 26 and 29, computer operated to apply the various 27 and 30 drop applications in the successive computerized requisite aligned patterns of the cross-sectional layers of the body 32 to be generated. The number and size of the ink jet printer's nozzles, as well as their size and a continuous supply means to "ink" cartridges (for practicing invention instead of the ink now supplying cartridges with and employing cartridges containing the liquid reactant-containing compositions for drops 27 and drops 30) is believed to be readily accomplished without undue experimentation by one of skill in the art to accommodate and to apply the respective discrete drops 27 and 30, respectively, at their desired and requisite pattern locations for creation of successive cross-sectional layers.

Useful reactants for inclusion in the liquid compositions which are to be dispensed as the initial drops and the subsequently applied drops include numerous and varied materials. As illustrative and not to be intended as limiting, there are taught the following:

For example, to generate an implantable non-load bearing prosthetic device of a calcium phosphate material, one employs, as compositions for the respectively applied and pattern distributed liquid drops, a liquid composition containing a calcium ion for one liquid drop and a liquid composition containing a phosphate ion for the another liquid drop with the ionic components of the two liquid compositions adapted upon contact to react to form a desired calcium phosphate prosthetic material. Illustrative substances for supplying the calcium ion include calcium chloride ($CaCl_2$), calcium hydroxide ($Ca(OH)_2$), and lime (CaO), and for supplying the phosphate ion include sodium monobasic phosphate ($NaH_2PO_4$), sodium dibasic phosphate ($Na_2HPO_4$), phosphoric acid ($H_3PO_4$), potassium monobasic phosphate ($KH_2PO_4$), and potassium dibasic phosphate ($K_2HPO_4$), etc., with water employed for the liquid. In some instances the water may be made mildly acidic, such as by inclusion in the water of minor amounts of phosphoric, hydrochloric or other acids or even some basic substances compatible with reaction of the particular ionic reaction between the particular calcium and phosphate ions contained in the liquid compositions.

Continuing further with useful liquid compositions for the drops for generating a structural body useful for prosthetic and like utilities, a structural body for such utilities desirably contains a significant bio-compatible content of $Ca_5(PO_3)OH$(hydroxyapatite).

Methods for providing a content of hydroxyapatite in the generated body include a supersaturating of the reactant-containing fluid compositions providing the first and second drops with dissolved hydroxyapatite, and/or suspending fine particles of hydroxyapatite therein, and/or alternatively an employing of reactants which upon reacting will form directly hydroxyapatite or form a precursor phosphate composition, capable upon a subsequent processing to form hydroxyapatite, such as by the conversion technology practical in the production of replamine form from calcium carbonate coral, when the invention's generated body contains significant precursor content of calcium carbonate. For example, for preparing hydroxyapatite from skeletal carbonate by hydrothermal exchange, see "Nature" Vol. 27 Jan. 25, 1974, p. 41–43.

To illustrate one hydroxyapatite supplying practice, one may employ any of numerous known reactions for preparing hydroxyapatite. Illustrative thereof one liquid composition for providing of drops containing $Ca_4(PO_4)_6.5H_2O$ (tetracalcium phosphate) for its reactant and the other liquid composition for providing drops containing for its other reactant any of various other calcium phosphates, namely $CaHPO_4.2H_2O$ (dicalcium phosphate dihydrate or brushite), $CaHPO_4$ (monetite), $Ca_8H_2(PO_4)_6.5H_2O$ (octacalcium phosphate), $\alpha\text{-}Ca_3(PO_4)_2$, $\beta\text{-}Ca_3(PO_4)_2$ (tricalcium phosphates), or tricalcium phosphates modified by the addition of protons or up to approximately 10% magnesium by weight (whitlockite), or combinations of these calcium phosphates in the other liquid composition. A chemical reaction of the foregoing nature is taught in U. S. Pat. No. 4,518,430, W. E. Brown et al., except that the patent's composition includes all phosphate reactants in single slurry or paste composition for useful applications as remineralizers of caries lesions in dental enamel and as dental cements and the like applications. In contrast, for practicing the instant invention, the tetracalcium phosphate reactant and the other reactant(s) are distributed one in one drop's liquid composition and the other in the other drop's liquid composition with the respective various drop placements of a size and applied under conditions adapted for reactant reaction, such as with a force adapted to mix already applied drops with the another applied contacting drops for the reaction between the phosphate reactants to proceed within a reasonable time to provide hydroxyapatite.

Although herein to now for practicing the invention the placed drops have been described as from one liquid composition and from an other liquid composition with each of the two liquid compositions containing a different ionic reactant of which the ionic reactants upon drop contacting react to provide cross-sectional layers successively built-up into the generated structural body comprised predominantly of the reaction product of the two ionic reactants, those particular invention practice(s) are intended to teach the presently preferred and best modes of practice of the invention. However, within the invention's scope are included "reactant-type" procedures and mechanisms wherein the following mediate and/or dominate a generation of the structural body:

(i) the one or both of the liquid composition and the other liquid composition for providing the respective drop placements may be at slightly sub-saturated or metastable concentrations and the secondly placed drops may include an ionic material of one or both of the reactants, or nucleated crystallites or seed crystals of the ionic constituents, to raise the concentration(s) in the contacting drops to a supersaturated condition(s) thereby causing a spontaneous crystal growth;

(ii) the composition of the applied drops of the first liquid composition may be of a metastable condition and the contacting of the first applied drops is by drops of the other liquid composition which contains an agent or constituent in an amount adapted upon the contacting to shift the supersaturation in the first applied drops to a no longer metastable state so that crystal and/or precipitate growth occurs. Useful for such destabilization are agents and constituent substances, such as acidic and/or basic substances, for example HCl, NaOH, $Ca(OH)_2$, CaO, $H_3PO_4$, and the like to change pH, or substances for example NaCl, to alter ionic strength of reactant(s);

(iii) the placed drops of one of the first or other or a third et al. liquid composition are at a stable condition and later or first placed drops include a catalytic agent, such as a free-radical initiator, for example benzoyl peroxide for drops containing reactants acrylonitrile or methacrylic acid, or vinyl chloride, so as to selectively convert the drops or reactant(s) in drops not containing the catalytic agent to solid constituent or an insoluble constituent, for example polyacrylonitrile; and (iv) one or both of the successively deposited drops of a composition may contain a polymeric constituent or other substance so as to: modify and/or regulate supersaturated conditions in the applied drops; or modify and control viscosity of the drop's liquid composition to facilitate drop placement; or serve as a distributed reinforcing agent and/or binder (either permanent, or fugitive to be subsequently removable, such as by a post process step,) or to modify and/or control, for example, mechanical, electrical, optical and the like properties of the generated structural body or to enhance its end utility application, such as by including collagen, to enhance its biocompatibility for implant purposes. Illustrative polymeric materials or other substances with a purpose for their inclusion in the one and/or the other liquid composition include: dispersants, such as a sodium salt of a polymethacrylate, wetting agents such as sulphated/sulphonated castor oil; particle binders, such as polyvinyl alcohols or the polyethylene glycols; viscosity control additives including natural macromolecules, such as collagen, gelatin, egg albumin and synthetic polymers such as polyalkoxylated aliphatic ethers; and anti-foaming agents, such as ethoxylated castor oil.

From the step 12 and 12' of drop-by-drop technique for generation of successive cross-sectional layers which eventually build-up together and are integrated into a green strength structural body 32', one in some instances, when desired and/or desirable, optionally may proceed with a post-treatment 13 and 13' process step (FIGS. 1 and 2) of green strength structural body 32' to provide a body 32" having one or more advantageous properties over body 32'. As already mentioned, for example: with calcium phosphates, hydroxyapatite, and several ceramic oxide particulate products of the drop's reactants all integrated into the generated three-dimensional body, a heating and/or post-firing treatment in an oven or furnace is useful. Firing treatments such as gradually raising the temperature of the green body 32' over a period of time up to a temperature between 1000° to 1200° C. and then maintaining this higher temperature for from ½ to 2 hours will provide a body 32' of enhanced strength by a sintering and binding together of integrated particulates comprising body 32". Likewise, if a heat-activatable water-soluble polymeric adhesive binder is included in a liquid composition for drops 27 and/or 30 and then is present in body 32', a heating of body 32' to a requisite temperature and for a requisite time to activate the heat-activated adhesive binder is desirable as a post treatment.

Although, as just described, a customary practice of the invention places a pattern of drops of a first liquid composition and then places, contacting those drops, drops of another liquid composition so that one or more reactants in the drops react to form a solid to comprise the cross-sectional layer of the body being formed, there may be placed even additional drops of additional liquid compositions so as to provide solids formed by any number of reactants in the two, three, four, or more liquid compositions placed as contacting drops. Noteworthy various applied drops may contain more than a single reactant. For example, various drops may contain various individual reactants adapted to react to provide inorganic solid, and the same or other applied drops may contain additional other reactants adapted to provide another solid (e.g. a resinous binder substance) which serves in part as a solid component comprising the cross-sectional layer of the body being prepared. Likewise such third and fourth, etc., applied drops, in addition to reactants, may contain other substances, as described herein, such as catalysts, inhibitors, fillers, binders, etc.

EXAMPLE I

The following provides an illustrative example which primarily by manual technique (rather than by CAD and CAM) presents a practice of the invention.

Preparation Of Metastable Liquid Compositions For Employment As Drops

A 0.75M $CaCl_2$ solution was prepared at room temperature by magnetic-stir-mixing 41.6 g of desiccant-grade $CaCl_2$ into 500 ml of distilled $H_2O$ until dissolved (approximately 20 minutes).

A 0.5M $Na_2HPO_4$ solution was prepared by mixing 35.4 g of reagent-grade $Na_2HPO_4$ into 500 ml of $H_2O$ until dissolved (approximately 40 minutes).

In a separate beaker there was placed 400 ml of the prepared 0.5M $Na_2HPO_4$ solution and stir mixing thereof was commenced. While mixing, there was added slowly, as a thin stream 486 ml of the prepared 0.75M $CaCl_2$ solution with a resulting suspension, a fine particle precipitate, being stirred for one hour. Mixing then was stopped and suspended particles were permitted to settle. After about one hour, the supernatant was decanted and the slurry restored to its original volume by adding distilled water and stir mixed for one hour. Again the suspension was permitted to settle; supernatant decanted; the slurry restored to its original volume by adding distilled water; and stir mixed for one hour before permitting the suspension to settle and with repetition of this washing procedure for two more times and with each decanting being of as much as practical of the supernatant water without losing settled precipitate, after each washing. Thereafter, the resulting settled aqueous composition containing the washed fine-particle precipitate was placed in centrifuge tubes and centrifuged at 10,000 rpm for five minutes and followed by excess liquid being decanted. The resulting product was an aqueous white glossy paste, which was stored as an aqueous paste until subsequently used. A small fraction of this paste was heat-dried and visually microscopically examined and found to be acicular crystals approximately 5–20 μm in length. The paste composition was not chemically analyzed but was an aqueous fine particle calcium phosphate precipitate of undetermined purity and composition.

Additional 0.5M reagent-grade $Na_2HPO_4$ aqueous solution was prepared as described earlier. A 0.86M desiccant-grade calcium chloride aqueous solution was prepared by the earlier described general procedure for preparation of the 0.75M $CaCl_2$ aqueous solution. Calf skin Type I collagen solution; specifically Pancogene-S® 0.3% acido-soluble solution; was utilized as the collagen source. Prior to use the collagen solution was dialized with dilute HCL solution at a pH of 2–3. The dialized solution provided 3 mg. collagen per ml. of dialized solution.

Slightly sub-saturated or metastable liquid suspensions were prepared as follows:

A first suspension was made by mixing 2 ml of the prepared 0.86M $CaCl_2$ aqueous solution, 2 ml of the prepared aqueous white glossy paste of fine particle calcium phosphate precipitate, and 1 ml of the prepared collagen/ HCL solution.

A second suspension was made by mixing 2 ml of the prepared 0.5M $Na_2HPO_4$ solution, 2 ml of the prepared aqueous white glossy paste of fine particle calcium phosphate precipitate, and 1 ml of the prepared collagen/HCL solution.

Two solutions were prepared as follows:

A first solution was prepared by mixing 2 ml of the prepared 0.86M $CaCl_2$ aqueous solution and 1 ml of the prepared collagen/HCL solution.

A second solution was prepared by mixing 2 ml of the prepared 0.5M $Na_2HPO_4$ solution and 1 ml of the prepared collagen/HCL solution.

A number of 10 μl pipettes and tips were used.

I(A) Experimental Trial

On a glass plate a plurality of 10 μl drops of the first suspension were placed not touching each other, but close enough that a drop subsequently placed along side adjacent drops would contact and/or overlap. 10 μl drops of the second suspension then were placed in a manner to contact and connect the deposited drops of the first suspension. Lines of precipitate formed with ridges at the interfaces of contacting drops of the first and second suspension. Observations at 70× magnification showed acicular crystals with a 4:1 aspect ratio had formed. The ridges appeared to be of denser crystals than crystals also noted in the central region of the drops.

A like depositing of successive drops of the first and second suspensions was made with the order of placing drops down being reversed so that drops of the phosphate ion suspension were laid down first and then subsequently connected by laying down drops of the calcium ion suspension.

The order of placements of the two suspension's drops appeared to make no difference in the resulting ridged solid-like structures which formed, except that a collagen film was wider around drops laid down first than around the drops laid down second. The ridge formations at drop interfaces appeared to be a primary site for calcium phosphate formation and precipitation to occur upon the drops of the first and second differing suspension compositions contacting and interacting upon the inter-drop contact-mixing occurring. The collagen content of the drops apparently serves to confine most of the formed precipitated crystals to be located at or near drops' interfaces and to be denser in nature than crystals formed in the drop's interior region by crystallization as the water from the various drops gradually dissipated (e.g. by room-temperature evaporation).

I (B) Experimental Trial

Using the first and second prepared solutions in place of the first and second prepared suspensions employed in I(A), the experimental procedure of the I(A) experimental trial was repeated with 10 μl drops of the first solution deposited in a plastic petri dish and with spacing between deposited individual drops being close enough that subsequently deposited drops of the prepared second solution would connect the first deposited adjacent drops by contacting sides of the first deposited drops and/or slightly overlapping the individual first deposited drops. As in the I (A) experimental trial, there also was made successive individual separate drops placement with the order of placement of drops from the first and second solutions being reversed. As in I(A) lines of crystalline precipitate formed at interfaces of adjacent drops upon the secondly deposited drops contacting or overlapping the firstly deposited drops. Observations at 70× showed a formed crystalline fibrous matrix interlaced with fine precipitated crystals.

Comparison of the results of I (A) and I (B) indicates a presence of suspended and solubilized $Na_2HPO_4$ in the placed drops does not greatly influence whether ridges are formed at contacting drop interfaces. Results also lead to hypothesizing that an alternating placement of counterion drops to greatly overlap and/or on top of the previously placed drops could result in a less-ridgelike and more fully integrated and connected lattice of crystal particles to provide a more desirable FFM relatively uni-planar layer for a being prepared body.

I(C) Experimental Example

Three-dimensional FFM structures or bodies were prepared as follows:

(i) On the bottom surface of a plastic petri dish there was placed a sequence of 10 μl-size drops of the prepared first suspension (i.e. containing $CaCl_2$) with the drops spaced adjacent to each other, but less than one-drop size spacing between the nearest drop(s). Then 10 μl-size drops of the prepared second suspension (i.e. containing $Na_2HPO_4$) were placed to connect deposited adjacent drops of the first suspension. A setting time between 10 to 15 minutes was permitted to elapse to permit the first created layer to set (i.e. for the $CaCl_2$ and $Na_2HPO_4$ drops to react and for some water to dissipate, such as by evaporation). Thereafter, on top of the first created layer there was laid down another sequence of 10 μl-size drops of the prepared first suspension with the drops spaced less than one-drop size spacing between drops and followed by application of 10 μl-size drops of the prepared second suspension to connect these just-applied first suspension drops with the whole of the first layer and second layer on top thereof permitted to set for 10 to 15 minutes. Then a third layer was laid down on top of the second layer in the same manner as the second layer was placed on the first, and followed by successive layer placing being continued until a total of five layers had been applied with the resulting integrated layered structural body now being free-standing and about 0.25 in. (6.4 mm) high, which calculates that each generated layer approximated about 0.05 in or 1.2 mm in thickness.

The layered structural body formed easily and held a free-formed structural shape. When the underlying layers were relatively dry (air-drying) the bulk of underlying ceramic would absorb liquid from freshly placed drops for creation of the next layer. This facilitated drop placement and localization, as viscosity appeared to increase rapidly in freshly applied drops upon application and also facilitated the precipitated crystals to be generated at very localized locations. When a body was relatively wet or moist, the placing of fresh drops and maintaining their desired locations was difficult since water was not removed quickly from freshly added drops by capillary action of the support layer. With relatively wet or moist underlying support layer or layers, freshly applied drops tended to spread (e.g. first layer) and/or flow down the sides (second and subsequent layers), but this spreading and flowing was controllable by applying fresh drops only to a relatively dry partially-formed structure and/or increasing viscosity of the drop's fluid suspension, such as by the amount and type of added viscosity enhancer (e.g. collagen) included in the fluid compositions. After several layers were accumulated, ridges such as noted in the uni-layer applications, I(A) and I(B) experimental trials, appeared to minimize and the formed layer was a smoother accretion of deposited-formed crystals plus crystals from the suspended and dissolved material in the drops upon the water dissipating. When the layered structural body which was formed was permitted to air dry, it had reasonable strength for mild handling but could be broken by bending, dropping, etc.

(ii) Subsequently other free-formed multi-layered structural bodies were prepared as described in (i) except that the bottom of the petri dish first was covered with a hand-smoothed layer of the previously described prepared aqueous white glossy paste of fine particle calcium phosphate precipitate which was air-dried after placement in the dish, to provide an initial porous support, before first drops application was made for the initial layer creation. In this manner a selective pattern of discrete drops for first and subsequent layer application(s) was better made and localized with minimizing and/or avoiding drop spreading and flowing from a desired pattern for the prepared cross-sectional layer(s).

With a relatively dry porous $Na_2HPO_4$ base layer in the petri dish, there subsequently were prepared additional free-standing vertical layered structural body shapes, including vertical columns, cantilever pillars (both from employing the first and second suspensions with and without a collagen content therein).

A truncated 4-sided hollow pyramid, several inches (750 mm) in height and about 1.5 in (~35–40 mm) base per side dimension also was made. The formed cantilevered pillars from drops not containing collagen, after reaching ¼ to ½ in (6.8 mm to 12.4 mm) in height, tended to break while wet under their own weight, while other shapes including vertical columnar pillars and the pyramid did not. Subsequently, an air drying of the prepared bodies gave bodies having reasonable strength for mild handling.

If greater strength is desired, the air-dried created bodies can be kiln-fired to 1100° C. to 1300° C. for 1 to 5 hours to provide a fused and/or sintered stronger bodies. Heat-fused and/or sintered created bodies are useful electrical conduit insulators in flat, columnar, tubular, ring, and the like shapes.

EXAMPLE II

One proceeds herein by following the general procedure and techniques taught in Example I unless noted otherwise.

Hydroxyapatite crystals are prepared as taught by T. Aaba and E. C. Moreno in *J. Dent. Res.*, June, 1984, pp. 874–880, and utilized in place of the Example I prepared aqueous fine particle calcium phosphate precipitate of undetermined purity and composition.

The prepared hydroxyapatite crystals, while still moist, and as replacement for the calcium phosphate precipitate of Example I, are dispersed as seed for crystallization in each of the first suspension and the second suspension with the first and second suspensions each containing amounts of the seed to supersaturate so as to provide metastable supersaturated fluid compositions.

Thereafter, discrete drops of the first suspension are applied in a line pattern to a porous support and followed by applying discrete drops of the second suspension overlapping adjacently placed drops of the first suspension and with this sequence of drop placements repeated successively for requisite times to build a three-dimensional structural green body of a vertical wall about 0.25 in (6.4 mm) wide to a height of 1 in (25.4 mm) which wall comprises a significant amount of hydroxyapatite seed crystals surrounded by calcium phosphate precipitate formed by reaction of the calcium chloride in the first suspension's drops with the $Na_2HPO_4$ content of the second suspension's drops. The thus fabricated wall-like and somewhat porous body also contains collagen and is contemplated to be useful in restorative surgery as a non-load bearing bone implant in animals. For greater strength before some usages the generated green body is fired at 1100° to 1200° C. for about 1 hour.

EXAMPLE III

There follows an illustration of a practice of a method of the invention, which includes CAD and CAM technology throughout and is contemplated to be a relatively ideal practice of the invention.

As illustrated in FIGS. 1 and 2, the initial step 10 and 10' respectively, is practiced to create and/or visualize a model of the object or body to be generated or created with CAD technology and techniques employed for the creation and visualization. The CAD generated model then by CAM computer technology and programming is subjected to the step, 11 and 11' respectively, of creation of a computer file of cross-sectional adjacent sliced layers of the CAD-generated model. Thereafter, the essential procedural sequence step, designated 12 and 12' respectively, is performed of physically generating and integrating the CAD generated and filed of adjacent sliced layers of the model into the laminar-like fabricated or created structural body. In this step CAM technology is employed to specify, control and regulate various procedural parameters, such as drop size, drops placement, support locations for successive drop placements and successive cross-sectional layer creations, etc. through connection to one or more modified "bubble-jet" ink jet printer(s), upon whose carriage(s) there travels controlled "ink" modified cartridges, one cartridge adapted to contain a liquid composition containing dispersed particles and a reactant and the second following cartridge adapted to contain dispersed particles and the other reactant for dispensing drops in patterned configurations to create successive cross-section layers. Modifications (not illustrated) in the modified ink jet printer(s) include, in place of the usual paper feed mechanism, a movable support base 20 having mounted thereon a porous support base 23 along with ancillary elements for base location and movement, such as described earlier, and with CAM technology employed to control and emulate the positioning and location of porous support base 23 in relation to the travelling controlled cartridges and drops placement. Envisioned is an optical encoded X-Y-Z table capable of moving the deposition head in an X-Y plane relative to the base. Manufacturers of this type of equipment claim they can position a moving head anywhere in this plane to ±2 µm precision.

In this manner there are prepared self-supporting or free-standing three-dimensional unitary structural bodies.

At the conclusion of the 12 or 12' step several created bodies are of immediate utility, depending on their composition and/or end utility, while others require a post-treatment step, generally designated 13 and 13' respectfully, before possessing requisite properties for their ultimate useful application.

EXAMPLE IV

By altering the feed liquid compositions in the drop-application system, it is expected that three-dimensional bodies of other synthetic compositions can also be manufactured according to the invention. As an example, the incorporation of alumina particles could be suspended in an acidic aqueous solution of dissolved aluminum salts. This would comprise composition 1. Composition 2 could be an aqueous ammonium hydroxide solution which would also contain alumina particles. By the reaction of these two drops alumina particles could be deposited on to a surface, while aluminum hydroxide particles would be precipitated from the reaction of the two solutions. Upon completion of the formed body a heat treatment could be used to oxidize the aluminum hydroxide precipitate to alumina. As alumina is electrically resistive this is an excellent way to manufacture a three-dimensional circuit board as opposed to the two-dimensional and surface mount circuit board currently being manufactured. A three-dimensional circuit board is a device that has conductive paths running through its volume as opposed to only on its surface. A three-dimensional board uses space more efficiently than the typical two-dimensional boards.

The advantage of this formation process is illustrated in the above description by creating drop by drop layers and layer by layer main bodies. Normally exotic features are incorporated automatically into the board. For example, instead of leaving holes where a conducting wire should go, a copper slurry, from a third deposition head, could be deposited that will provide a conducting path when post forming heat treatments are applied. A post heat treatment will not only densify the ceramic material but would fuse the copper powder into a single conductor. If desired, a fourth head could deposit a thermally conductive material, such as berylia or aluminum nitride to remove heat away from delicate electrical components along the thermal conductor to an outside heat sink.

Alumina, silica, barium titanate, or other materials that have suitable electrical properties are contemplated as useful in this type of application. Useful structures that could be generated include angles that cut back on themselves, channels that are wide at the bottom, narrow at the middle and wide at the top, three-dimensional pathways and variable composition within a single layer of a laminated structure.

This illustrative example serves as an application of the invention's technology and gives rise to other applications which could include functionally gradient materials that are ceramic on one side and metal on the other side and which could find use as liners for piston barrels in a ceramic engine, piezoelectric actuators and transducers, capacitors, and even optics.

EXAMPLE V

An additional example would employ the herein taught successive drop application system to prepare three-dimensional bodies of synthetic resinous polymer compositions which include not only those bodies comprised in part of a synthetic resinous polymer but also those bodies which consist essentially or entirely of a synthetic resinous polymer formed by polymeric component reactants reacting in situ to form the three-dimensional body.

As illustrative thereof one would place a pattern of discrete drops of a first liquid composition containing a component reactant for the resinous polymer and overlay these placed drops with contacting discrete drops of one or more other liquid compositions containing one or more other component reactants for the resinous polymer. The various component reactants in the variously applied drops, after contacting each other, with or without reaction initiation by other components contained within the drops and/or means applied to the drops during and/or after placement then would proceed to react to form a synthetic resinous polymer. In this manner one generates successive cross-sectional layers of the body one on top of another, which cross-sectional layers, as created, are integrated and joined to form a laminar or layered-type three-dimensional synthetic polymeric body comprised completely or only in part, as desired, of synthetic resinous polymer formed in situ.

As illustrative thereof, for example: one employs for the various applied drops various successive liquid compositions known to the art as two-component reactant compositions, each of the reactant components being in a separate liquid composition, to react rapidly to provide a solid epoxy resin; or various two- and three- component reactants in two or more of the liquid compositions providing the drops, known to the art as capable to react rapidly to provide a solid urethane or epoxy-urethane resin.

With greater particularity, for example, a liquid composition 1 contains epichlorohydrin and is used to provide discrete drops containing epichlorohydrin. Then a liquid composition 2 containing Bisphenol A® is applied as contacting drops containing the Bisphenol A® so that the epichlorohydrin and Bisphenol A® react to provide a cross-sectional layer of an epoxy polymeric resin as a laminar layer of the being prepared three-dimensional body. Subsequent successive drop placement repetitions repeated successively one on top of another generate and build-up a plurality of generated cross-sectional layers into the prepared three-dimensional body comprising epoxy polymeric resin. Epichlorohydrin and Bisphenol A® provide reaction products of glycidyl ether resins characterized by the presence of the epoxy (oxirane) group. By appropriate selection, as known in the art, of an employed ratio of the reactants of epichlorohydrin and Bisphenol A, their reaction product is provided as an epoxy resinous solid of significant molecular weight. Since the reaction is exothermic, not illustrated auxiliary means for cooling, such as solvent evaporation with fan and duct means to conduct solvent vapors away from the formed layer, may be utilized, if needed or desired, so that repetitive cross-sectional layer preparations may proceed relatively rapidly. The liquid in the liquid compositions containing the epichlorohydrin and Bisphenol A® generally is an organic liquid, desirably an alcohol, in that the reactant components are soluble in oxygenated solvents, as ketones, esters, ether alcohols and alcohols, while solid epoxy resins are usually not soluble in alcohols, aliphatic hydrocarbons and aromatic hydrocarbons. Of course, the liquid compositions for drop applications may contain other reactant modifiers suspended filler particles (such as silica, aluminum, etc.) known catalysts and hardeners in requisite amounts to speed the course of the reaction, as well as other appropriately sized particulate materials known to be useful in preparation of cast-bodies and the like of epoxy resin polymers.

As illustrative and of greater particularity for preparing a three-dimensional structural body comprising a polyurethane resinous solid, a liquid composition 1 contains a polyisocyanate and as discrete drops thereof is deposited in a desired pattern, and then overlaid by placing thereon discrete contacting drops of a liquid composition comprising a polyol, such as a polyether polyol (mol. wt. 1000–4000), or a linear or branched polyester polyol (mol wt. 500–5000) for a coreactant with the polyisocyanate. Upon reaction of the polyol coreactant and the polyisocyanate to provide solid reaction product there is obtained a cross-sectional layer of a polyurethane resinous polymer. Subsequent successive drop placement repetitions repeated successively one on top of the other make and build-up a plurality of generated cross-sectional layers into the three-dimensional body comprising polyurethane resinous polymer. Particularly useful for polyisocyanate component reactant in the liquid composition 1 are a polyisocanate adduct of toluene 2,4-disocyanate (TDI) with a trifunctional alcohol, e.g. trimethylolpropane, followed by excess monomeric TDI distilled off to reduce the monomeric contained TDI to a concentration of less than 1%. Another illustrative useful polyisocyanate is a biuret of hexamethylene disocyanate (HDI) obtained by reaction of 3 moles of HDI with water or other biuretting agent in presence of excess HDI followed by removal of the excess HDI. As with the preparation of the just described three-dimensional body of epoxy resin polymer, a variety and large number of liquids and other components and substances may be used in the various liquid compositions, containing the various polyisocyanate and polyol coreactants reacting to provide polyurethane resinous solid. Thus, the liquid solvent compositions containing the various coreactants providing the polyurethane in addition to liquid and coreactants may include, for example, binder, pigment, fillers and additive substances, such as catalysts, moisture scavengers, flow aids or flow retardants, etc., as desired or needed, provided each is of a size not interfering or preventing the drop applications. Common useful liquids also are solvents for one or more of the coreactants and include esters, ketones, ether-esters, and aromatic solvents, such as toluene, xylene, and petroleum distillates having low moisture contents to avoid reaction of water with the isocyanate reactant. Pigments, fillers, colorants and other substances customarily included in polyurethane coatings and the like also can be included in the liquid compositions containing the polyol and polyisocyanate reactants.

Because of the desirable physical and chemical properties of prepared three-dimensional bodies comprised of synthetic resinous polymer, these bodies may take the structures of and be useful not only as prototype models of various parts or articles of manufacture for which evaluation or testing is sought, but these bodies are contemplated as useful as patterns, molds for casting, etc.

It is to be understood that the foregoing disclosure, including examples, only emphasizes a few specific and illustrative embodiments of the invention and that within the true spirit and scope of the invention are all obvious and/or equivalent modifications and alternatives thereof.

While certain preferred embodiments of the present invention have been disclosed in detail, it is to be understood that various modifications may be adopted without departing from the spirit of the invention or scope of the following claims.

We claim:

1. A method for a free-form preparation of a free-standing three-dimensional structural body by successively generating adjacent cross-section layers of the body with a freshly generated layer generated on top of a previously generated layer and with previously and freshly generated adjacent layers integrated to comprise the free-standing three-dimensional structural body, which method comprises: successively repeating the steps of:

a) placing a plurality of individual liquid drops of a liquid composition on a support surface as discrete individual drops arranged in a pattern corresponding to a cross-sectional layer of the body being prepared and positioned within the pattern so as to be non-contacting, and with the liquid composition containing a first reactant;

b) placing a plurality of discrete individual liquid drops of an other liquid composition in said pattern of the cross-sectional layer of the body being prepared with the depositing of the discrete individual drops of the other liquid composition positioned within said pattern so as to contact and connect non-contacting deposited drops of the liquid composition, and with the other liquid composition containing an other reactant adapted after contacting the first reactant to chemically react therewith to form a solid which comprises the cross-sectional layer of the body being prepared.

2. The method of claim 1 in step (a) of employing the support surface of a previously generated cross-sectional layer of the body.

3. A method in which claim 2 is repeated successively until there is an integrated accumulation of prepared cross-sectional layers to comprise the free-standing three-dimensional structural body.

4. The method of claim 1 employing in an initial practice of step (a) for the support surface of a porous solid support surface adapted to absorb liquid from liquid droplets deposited thereon.

5. The method of claim 1 employing a step (c), in addition to and following steps (a) and (b), and comprising:

(c) placing a plurality of discrete individual liquid drops of at least a third liquid composition in said pattern of the cross-sectional layer of the body being prepared with the depositing drops of the third liquid composition positioned within said pattern so as to not contact or to contact one to more of the deposited drops of steps (a) and (b) or a mixture of the drops deposited by steps (a) and (b) with the at least third liquid composition containing one to more of (i) a third reactant adapted upon contacting the first and the other reactant to react therewith and to form a solid, (ii) a catalyst upon contacting the mixture of the drops deposited to initiate and/or accelerate the speed of reaction between the first reactant and the other reactant or between the first reactant, the second reactant and the third reactant, and (iii) a substance other than a first, second or third reactant and with drops containing the substance positioned so as to provide conducting passages in the body being prepared and with the substance as deposited or after a post treatment being a heat or electrical conductor.

6. A method for a free-form preparation of a free-standing three-dimensional structural body by successively generating adjacent cross-section layers of the body with a freshly generated layer generated on top of a previously generated layer and with previously and freshly generated adjacent layers integrated to comprise the free-standing three-dimensional structural body, which method comprises: successively repeating the steps of:

a) placing a plurality of individual liquid drops of a liquid aqueous composition on a support surface as discrete individual drops arranged in a pattern corresponding to a cross-sectional layer of the body being prepared and positioned within the pattern so as to be non-contacting, and with the liquid aqueous composition containing a first reactant;

b) placing a plurality of discrete individual liquid drops of an other liquid aqueous composition in said pattern of the cross-sectional layer of the body being prepared with the depositing of the discrete individual drops of the other liquid aqueous composition positioned within said pattern so as to contact and connect one or more non-contacting deposited drops of the liquid aqueous composition, and with the other liquid aqueous composition containing an other reactant adapted after contacting the first reactant to chemically react to form an inorganic solid which comprises the cross-sectional layer of the body being prepared.

7. The method of claim 6 in step (a) of employing the support surface of a previously generated cross-sectional layer of the body.

8. A method in which claim 7 is repeated successively until there is an integrated accumulation of prepared cross-sectional layers to comprise the free-standing three-dimensional structural body.

9. The method of claim 6 employing in an initial practice of step (a) for the support surface of a porous solid support surface adapted to absorb liquid from liquid droplets deposited thereon.

10. The method of claim 6 employing a step (c) in addition to and following steps (a) and (b), and comprising:
    (c) placing a plurality of discrete individual liquid drops of at least a third aqueous liquid composition in said pattern of the cross-sectional layer of the body being prepared with the depositing drops of the third aqueous liquid composition positioned within said pattern so as to not contact or to contact one to more of the deposited drops of steps (a) and (b) or a mixture of the drops deposited by steps (a) and (b) with the at least third aqueous liquid composition containing one to more of
    (i) a third reactant adapted upon contacting the first and the other reactant to react therewith and to form a solid,
    (ii) a catalyst upon contacting the mixture of the drops deposited to initiate and/or accelerate the speed of reaction between the first reactant and the other reactant or between the first reactant, the second reactant and the third reactant, and
    (iii) a substance other than a first, second or third reactant and with drops containing the substance positioned so as to provide conducting passages in the body being prepared and with the substance as deposited or after a post treatment being a heat or electrical conductor.

11. The method of claim 10 in which one or more of the liquid aqueous solution, the other liquid aqueous solution and the third liquid aqueous solution contains dissolved, dispersed, or suspended solid particles of a substance which upon water depletion of the deposited drops remains to comprise a portion of the solid which comprises the cross-sectional layer of the body being prepared.

12. The method of claim 11 in which the dissolved, dispersed, or suspended solid particles are of a composition of the solid formed by reaction of the first and the other reactant or of the solid formed by reaction of the first reactant, the other reactant and the third reactant.

13. The method of claim 11 in which the dissolved, dispersed or suspended solid particles are of a composition different from solid formed by reaction of the first and other reactant and of solid formed by reaction of the first reactant, the other reactant and the third reactant.

14. The method of claim 6 in which each of the fluid compositions and the other fluid compositions contain ions and with ions contained in the solution adapted to react with contained different ions in the other solution and upon contacting to react to provide an inorganic solid.

15. The method of claim 6 employing $Na_2HPO_4$ and $CaCl_2$, respectively contained separately, one in the fluid composition and one in the other fluid composition.

16. The method of claim 15 in which each of the fluid composition and the other fluid composition also include particles of $Na_2HPO_4$ dissolved and suspended therein.

17. The method of claim 14 including in each of the solution and the other solution in addition to the ions of a dissolved viscosity-enhancing substance.

18. The method of claim 17 employing collagen for the dissolved viscosity-enhancing substance.

19. The method of claim 17 employing chondroitin sulfate D for the dissolved viscosity-enhancing substance.

20. A method of practicing claim 6 which includes the steps of:
    i) employing CAD technology to design the free-standing, three-dimensional structural body;
    ii) employing CAD technology to slice into requisite-size cross-sectional layers the design of the free-standing, three-dimensional structural body designed by employing CAD technology; and
    iii) employing CAM technology in practicing the (a) and (b) steps of claim 6.

21. The method of claim 8 employing a computer operated modified ink jet printer for the steps of (a) placing the drops of the liquid composition and (b) placing the drops of the other liquid composition.

* * * * *